US00PP24863P2

(12) United States Plant Patent
Groot

(10) Patent No.: US PP24,863 P2
(45) Date of Patent: Sep. 9, 2014

(54) POINSETTIA PLANT NAMED 'PER2109'

(50) Latin Name: ***Euphorbia pulcherrima* Willd.**
Varietal Denomination: PER2109

(71) Applicant: Dana J. Groot, Encinitas, CA (US)

(72) Inventor: Dana J. Groot, Encinitas, CA (US)

(73) Assignee: Ecke Ranch B.V., De Lier (NL)

( * ) Notice: Subject to any disclaimer, the term of this patent is extended or adjusted under 35 U.S.C. 154(b) by 0 days.

(21) Appl. No.: 13/694,961

(22) Filed: Jan. 22, 2013

(51) Int. Cl.
*A01H 5/00* (2006.01)

(52) U.S. Cl.
USPC ..... Plt./306

(58) Field of Classification Search
USPC ..... Plt./306
See application file for complete search history.

*Primary Examiner* — Anne Grunberg
(74) *Attorney, Agent, or Firm* — C. A. Whealy

(57) ABSTRACT

A new and distinct cultivar of Poinsettia plant named 'PER2109', characterized by its compact, uniform, upright and mounded plant habit; moderately vigorous growth habit; freely and upright branching habit; dark green-colored leaves; mid-season flowering response; under natural season conditions, plants flower in late November in Southern California; large inflorescences with dusty pink-colored flower bracts covered with light red-colored random speckles and splotches; and good post-production longevity.

1 Drawing Sheet

Botanical designation: *Euphorbia pulcherrima* Willd.
Cultivar denomination: 'PER2109'.

CROSS REFERENCED TO CLOSELY-RELATED APPLICATIONS

Title: Poinsettia Plant Named 'PER2009'
Applicant: Dana J. Groot
Filed: Concurrently with this application

BACKGROUND OF THE INVENTION

The present invention relates to a new and distinct cultivar of Poinsettia plant, botanically known as *Euphorbia pulcherrima* Willd., and hereinafter referred to by the name 'PER2109'.

The new Poinsettia plant originated is a naturally-occurring whole plant mutation of *Euphorbia pulcherrima* Willd. '490', disclosed in U.S. Plant Pat. No. 7,825. The new Poinsettia plant was discovered and selected by the Inventor as a single flowering plant from within a population of plants of '490' in a controlled greenhouse environment in Encinitas, Calif. in December, 2006.

Asexual reproduction of the new Poinsettia plant by terminal vegetative cuttings in a controlled greenhouse environment in Encinitas, Calif. since December, 2007 has shown that the unique features of this new Poinsettia plant are stable and reproduced true to type in successive generations of asexual reproduction.

SUMMARY OF THE INVENTION

Plants of the new Poinsettia have not been observed under all possible environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'PER2109'.

These characteristics in combination distinguish 'PER2109' as a new and distinct Poinsettia plant:

1. Compact, uniform, upright and mounded plant habit.
2. Moderately vigorous growth habit.
3. Freely and upright branching habit.
4. Dark green-colored leaves.
5. Mid-season flowering response; under natural season conditions, plants flower in late November in Southern California.
6. Large inflorescences with dusty pink-colored flower bracts covered with light red-colored random speckles and splotches.
7. Good post-production longevity.

In side-by-side comparisons conducted in Encinitas, Calif., plants of the new Poinsettia differ primarily from plants of the parent, '490', in flower bract color as plants of '490' have dark red-colored flower bracts with no flecking. In addition, plants of the new Poinsettia are more compact than and not as vigorous as plants of '490'.

Plants of the new Poinsettia can be compared to plants of the *Euphorbia pulcherrima* Willd. 'PER2009', disclosed in U.S. Plant patent application Ser. No. 13/694,964. Plants of the new Poinsettia and 'PER2009' differ primarily in flower bract color.

Plants of the new Poinsettia can also be compared to plants of the *Euphorbia pulcherrima* Willd. '3-91', disclosed in U.S. Plant Pat. No. 9,602. In side-by-side comparisons conducted in Encinitas, Calif., plants of the new Poinsettia differed primarily from plants of '3-91' in the following characteristics:

1. Plants of the new Poinsettia were more compact than and not as vigorous as plants of '3-91'.
2. Leaves of plants of the new Poinsettia were darker green in color than leaves of plants of '3-91'.
3. Plants of the new Poinsettia flowered about one week earlier than plants of '3-91' when grown under natural season conditions.
4. Plants of the new Poinsettia and '3-91' differed in leaf and flower bract shape.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph at the bottom of the sheet comprises a side perspective view of a typical flowering plant of 'PER2109' grown in a container.

The photograph at the top of the sheet is a close-up view of a typical flowering plant of 'PER2109'.

DETAILED BOTANICAL DESCRIPTION

Plants used in the aforementioned photographs and in the following detailed description were grown during the late autumn/early winter in 16.5-cm containers in a polyethylene-covered greenhouse in Encinitas, Calif. and under natural season conditions and cultural practices typical of commercial Poinsettia production. During the production of the plants, day temperatures averaged 24° C., night temperatures averaged 18° C. and light levels averaged 5,000 foot-candles. Measurements and numerical values represent averages for typical flowering plants. Plants were pinched one time and were 17 weeks old when the photographs and the description were taken. In the following description, color references are made to The Royal Horticultural Society Colour Chart, 2007 Edition, except where general terms of ordinary dictionary significance are used.

Botanical classification: *Euphorbia pulcherrima* Willd. 'PER2109'.

Parentage: Naturally-occurring whole plant mutation of *Euphorbia pulcherrima* Willd. '490', disclosed in U.S. Plant Pat. No. 7,825.

Propagation:

*Type*.—Terminal vegetative cuttings.

*Time to initiate roots*.—About one to two weeks at 20° C. night temperature and 27° C. day temperature.

*Time to produce a rooted young plant*.—About four weeks at 16° C. night temperature and 18° C. day temperature.

*Root description*.—Fibrous; white in color.

Plant description:

*Plant habit and form*.—Compact, uniform, upright and mounded plant habit; inverted triangle; large inflorescences positioned above the foliar plane; moderately vigorous growth habit.

*Plant height*.—About 35 cm.

*Plant diameter or spread*.—About 62 cm.

*Lateral branch description*.—Quantity: Freely branching habit, about eight lateral branches develop after pinching. Length: About 33 cm. Diameter: About 8 mm. Internode length: About 2.2 cm. Strength: Strong. Texture: Smooth, glabrous. Color: Close to 146B.

*Leaf description*.—Arrangement: Alternate, simple. Length: About 13 cm. Width: About 8.4 cm. Shape: Broadly lanceolate. Apex: Acuminate. Base: Rounded to nearly truncate. Margin: Mostly entire. Aspect: Flat. Venation pattern: Pinnate, arcuate. Texture, upper surface: Scattered pubescence. Texture, lower surface: Pubescent; prominent venation. Color: Developing leaves, upper surface: Close to 136A. Developing leaves, lower surface: Close to 137B. Fully expanded leaves, upper surface: Darker than 136A; venation, close to 137C. Fully expanded leaves, lower surface: Close to 137A; venation, close to 147C. Petiole: Length: About 6.5 cm. Diameter: About 2.5 mm. Texture, upper and lower surfaces: Smooth, glabrous. Color, upper surface: Close to N199C. Color, lower surface: Close to 195A.

Inflorescence description:

*Inflorescence type and habit*.—Terminal inflorescences are compound corymbs of cyathia with colored flower bracts subtending the cyathia; inflorescences uniformly positioned above the foliar plane.

*Fragrance*.—None detected.

*Flowering response*.—Mid-season flowering response; under natural season conditions, plants typically flower in mid to late November in Southern California; under artificial long nyctoperiod/short photoperiod conditions, plants flower about 8 to 8.5 weeks later.

*Post-production longevity*.—Good post-production longevity; plants of the new Poinsettia maintain good substance and flower bract color for about four weeks under interior conditions; inflorescences persistent.

*Inflorescence diameter*.—About 37 cm.

*Inflorescence height* (*depth*).—About 5.8 cm.

*Flower bracts*.—Quantity per inflorescence: About 20. Length, largest bracts: About 15.8 cm. Width, largest bracts: About 11.5 cm. Shape: Broadly lanceolate to elliptical. Apex: Acuminate. Base: Rounded. Margin: Entire. Texture, upper surface: Smooth, glabrous. Texture, lower surface: Veins prominent, glabrous. Aspect: Mostly horizontal, older bracts drooping with development. Venation pattern: Pinnate, arcuate. Color: Developing or transitional bracts, upper surface: Ground color, close to 145A to 145B tinted with close to 180C to 180D. Developing or transitional bracts, lower surface: Close to 145B to 145C. Fully expanded bracts, upper surface: Ground color, close to 48A; numerous random speckles and splotches, close to 47A to 47B; with development, ground color becoming closer to 158C with numerous random speckles and splotches, close to 48B; central bracts, close to 47A. Fully expanded bracts, lower surface: Ground color, close to 49A with flecks and speckles, close to 47C to 47D; color becoming closer to 160D with development. Bract petiole: Length: About 4.2 cm. Diameter: About 2.5 mm. Texture, upper and lower surfaces: Smooth, glabrous. Color, upper surface: Close to N34C. Color, lower surface: Close to 145B.

*Cyathia*.—Quantity per corymb: About 20. Length: About 1.1 cm. Width: About 8 mm. Shape: Ovoid. Texture: Smooth, glabrous. Color, immature: Close to 146A. Color, mature: Close to 146A to 146B.

*Nectaries*.—Quantity per cyathium: One or two. Length: About 6 mm. Width: About 4 mm. Shape: Elongated oval. Texture: Smooth, glabrous. Color: Close to 15B.

*Peduncles*.—Length: About 4 mm. Diameter: About 2.5 mm. Strength: Strong. Aspect: Mostly upright to outwardly. Texture: Smooth, glabrous. Color: Close to 144A.

*Reproductive organs*.—Stamens: Quantity per cyathium: About ten. Filament length: About 4 mm. Filament color: Close to 182B. Anther shape: Oval; bi-lobed. Anther length: About 1 mm. Anther color: Close to 183B. Amount of pollen: Scarce. Pollen color: Close to 12A. Pistils: Pistil development has not been observed on plants of the new Poinsettia.

*Seeds and fruits*.—Seed and fruit production have not been observed on plants of the new Poinsettia.

Disease & pest resistance: Plants of the new Poinsettia have not been shown to be resistant to pathogens and pests common to Poinsettia plants.

Temperature tolerance: Plants of the new Poinsettia have been observed to tolerate temperatures ranging from about 16° C. to about 29° C.

It is claimed:

1. A new and distinct Poinsettia plant named 'PER2109' as illustrated and described.

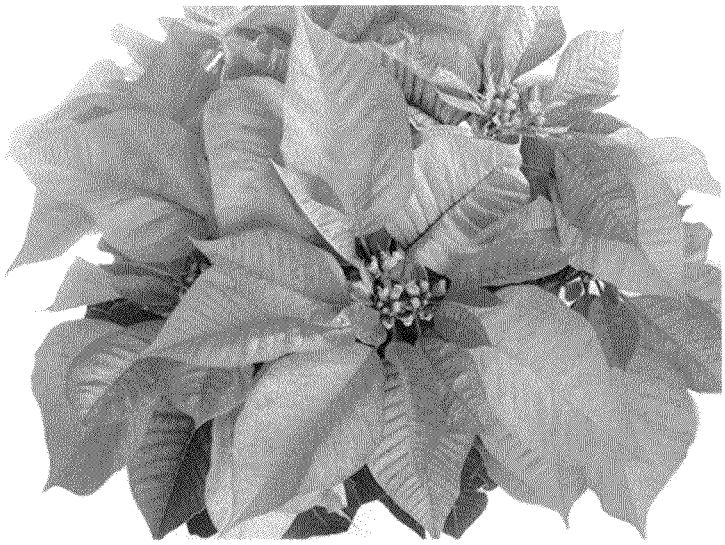
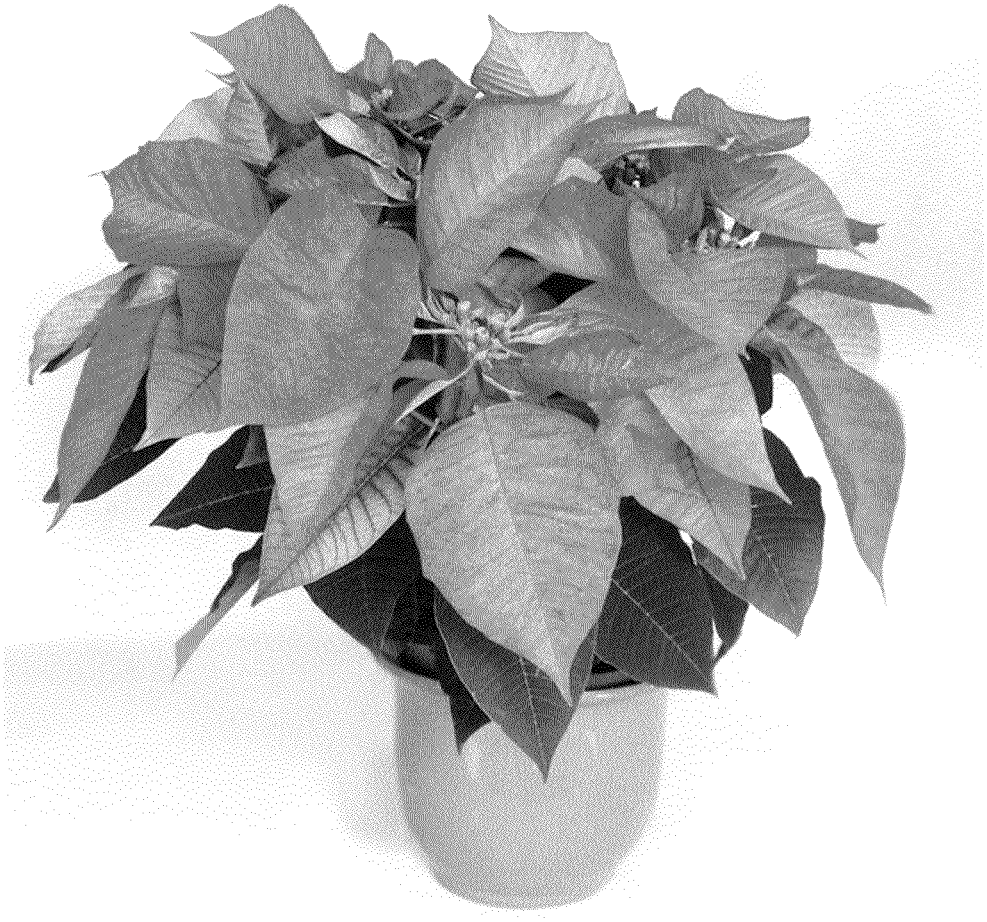

* * * * *